(12) United States Patent
Fogarty

(10) Patent No.: US 6,316,690 B1
(45) Date of Patent: Nov. 13, 2001

(54) NON-MAMMALIAN TRANSGENIC ANIMAL MODEL FOR CELLULAR PROLIFERATIVE DISEASES

(75) Inventor: Patrick Fogarty, San Mateo, CA (US)

(73) Assignee: Tosk, Inc., Santa Cruz, CA (US)

( * ) Notice: Subject to any disclaimer, the term of this patent is extended or adjusted under 35 U.S.C. 154(b) by 0 days.

(21) Appl. No.: 09/472,661

(22) Filed: Dec. 27, 1999

Related U.S. Application Data

(60) Provisional application No. 60/147,433, filed on Aug. 4, 1999.

(51) Int. Cl.$^7$ .................. A01K 67/00; A01K 67/033; G01N 33/00
(52) U.S. Cl. .................. 800/3; 800/8; 800/9; 800/10; 800/13
(58) Field of Search ................. 800/3, 8, 9, 13, 800/10

(56) References Cited

U.S. PATENT DOCUMENTS

| | | | |
|---|---|---|---|
| 4,670,388 | 6/1987 | Rubin et al. | 435/172.3 |
| 5,753,434 | 5/1998 | Ryner et al. | 435/6 |
| 5,972,639 | 10/1999 | Parandoosh | 435/29 |
| 5,994,503 | 11/1999 | Xu et al. | 530/350 |

FOREIGN PATENT DOCUMENTS

| | | |
|---|---|---|
| WO99/37672 | 7/1909 | (WO) . |
| WO99/55906 | 11/1999 | (WO) . |
| WO99/64586 | 12/1999 | (WO) . |

OTHER PUBLICATIONS

Komori M et al. Carcinogenesis 14:1683–1688, 1993.*
Watson KL et al. Journal of Cell Science, Supplement 18, 19–33, 1994.*
Woodhouse E. et al Dev. Genes Evol. 207:542–550, 1998.*
Fu and Lipsick, Journal of Virology 70:5600–5610, 1996.*
Michaud DS et al. J Natl Cancer Inst 91:605–613, 1999.*
Badiani PA. Oncogene 13:2205–2212, 1996.*
BIOSIS Accession No. 1997:249440, Fehon et al. (1997) "Isolation of mutations in the Drosophila homologues of the human Neurofibromatosis 2 and yeast CDC42 genes using a simple and efficient reverse–genetic method." *Genetics,* vol. 146(1):245–252. Abstract Only.
Lipsick et al. (1986) "The myb oncogene." *Gene Amplif Anal,* vol. 4:73–98. Abstract Only.
Schuh et al. (1999) "Mechanisms of disease and injury: utilization of mutants, monoclonals, and molecular methods." *Toxicol Pathol,* vol. 27(1):115–20. Abstract Only.
BIOSIS No. 000012062466, Vogel (1975) "Some Aspects of the Detection of Potential Mutagenic Agents in Drosophila." *Mutation Research,* vol. 29(2):241–250. Abstract Only.

* cited by examiner

Primary Examiner—Scott D. Priebe
Assistant Examiner—Ram R. Shukla
(74) Attorney, Agent, or Firm—Bret E. Field; Bozicevic, Field & Francis

(57) ABSTRACT

Non-mammalian, transgenic animals, e.g. flies, that exhibit neoplastic phenotypes, i.e. spontaneously produce metastatic tumors, are provided. Also provided are methods of using the subject transgenic non-mammalian animals to identify compounds having activity with respect to cellular proliferative, and particularly neoplastic, diseases. Finally, kits for screening compounds for anti-neoplastic activity are provided.

10 Claims, 1 Drawing Sheet wild-type larva

Tumorous larva
(Early/Middle stage
of tumor progression)

Tumorous larva
(Late stage of tumor
progression)

NON-MAMMALIAN TRANSGENIC ANIMAL MODEL FOR CELLULAR PROLIFERATIVE DISEASES

CROSS REFERENCE TO RELATED APPLICATIONS

Pursuant to 35 U.S.C. §119 (e), this application claims priority to the filing date of the U.S. Provisional Patent Application Serial No. 60/147,433 filed Aug. 4, 1999, the disclosure of which is herein incorporated by reference.

INTRODUCTION

1. Field of the Invention

The field of this invention is animal models of cellular proliferative diseases.

2. Background of the Invention

Cancer remains one of the leading causes of death in the United States. Clinically, a broad variety of medical approaches, including surgery, radiation therapy and chemotherapeutic drug therapy are currently being used in the treatment of human cancer (see the textbook CANCER: Principles & Practice of Oncology, 2d Edition, De Vita et al., eds., J. B. Lippincott Company, Philadelphia, Pa., 1985). With respect to chemotherapeutic drug therapy approaches, a broad variety of different types of active agents have been identified that exhibit anti-cellular proliferative activity, and some of these agents currently find use in the treatment of cancer and related cellular proliferative diseases. Agents which have been found to exhibit anti-cellular proliferative activity include: cytostatics, plant alkaloids, antibiotics, etc. However, despite the large number of compounds that have been identified to date, no ideal drug therapeutic has yet been discovered.

Critical steps in the identification and development of new therapeutic agents are: (a) generation of candidate agents; and (b) screening of the candidate agents for efficacy and safety. With the advent of combinatorial chemistry protocols, large numbers of potential compounds, known as libraries, can be rapidly generated. Such libraries serve as collections of potential therapeutic agents. Following generation of a library of potential therapeutic agents, the library must be screened to identity the promising candidates.

For screening purposes, a number of in vitro high throughput screening protocols have been developed. However, these in vitro screening assays must be followed by in vivo screening assays. Since it is undesirable to immediately screen compounds that show promise from in vitro assays in humans, an important step in the identification of therapeutic agents for such cellular proliferative diseases is the screening of potential therapeutic compounds in non-human animal models. As such, non-human animal models of cancer and other cellular proliferative diseases play an important role in the discovery of therapeutic agents for such diseases.

One type of non-human animal model that can be used for screening purposes to identify therapeutic agents for use in treating cancer and other cellular proliferative diseases is a non-human mammalian model, e.g. mice, etc. However, mice are expensive, have a slow reproduction time, and generate small numbers of offspring. As such, they are less than ideal for many high throughput screening assays.

Accordingly, there is a need for additional animal models of cellular proliferative, e.g. neoplastic, diseases. Of particular interest would be the development of an animal model having a relatively short life span and a rapid reproduction cycle characterized by the production of large numbers of offspring. Preferably, such an animal model should also be relatively simple and economic to maintain.

Relevant Literature

Of interest is: Woodhouse et al., Dev. Genes. Evol. (1998) 207:542–550. Methods of preparing transgenic Drosophila melanogaster are disclosed in: Spradling, A. C., and Rubin, G. M. (1982). Science 218, 341–347; Brand & Perrimon, Development (1993) 118: 401–415; and Phelps & Brand, Methods (April 1998) 14:367–379. See also, Spradling A C, P Element Mediated Transformation in Drosophila: A Practical Approach (ed. D. D. Roberts, IRL Press, Oxford)(1986) pp 175–179.

SUMMARY OF THE INVENTION

Transgenic non-mammalian animals, e.g. flies, that have a neoplastic phenotype, i.e. that spontaneously develop metastatic tumors, are provided. The subject transgenic animals are characterized in that they have a v-myb transgene stably integrated into their genome that is expressed in a manner that gives rise to the neoplastic phenotype. Also provided are methods of screening compounds for activity with respect to cellular proliferative disease conditions, particularly compounds having therapeutic activity with respect to neoplastic disease conditions.

DESCRIPTION OF THE SPECIFIC EMBODIMENTS

Figure 1:
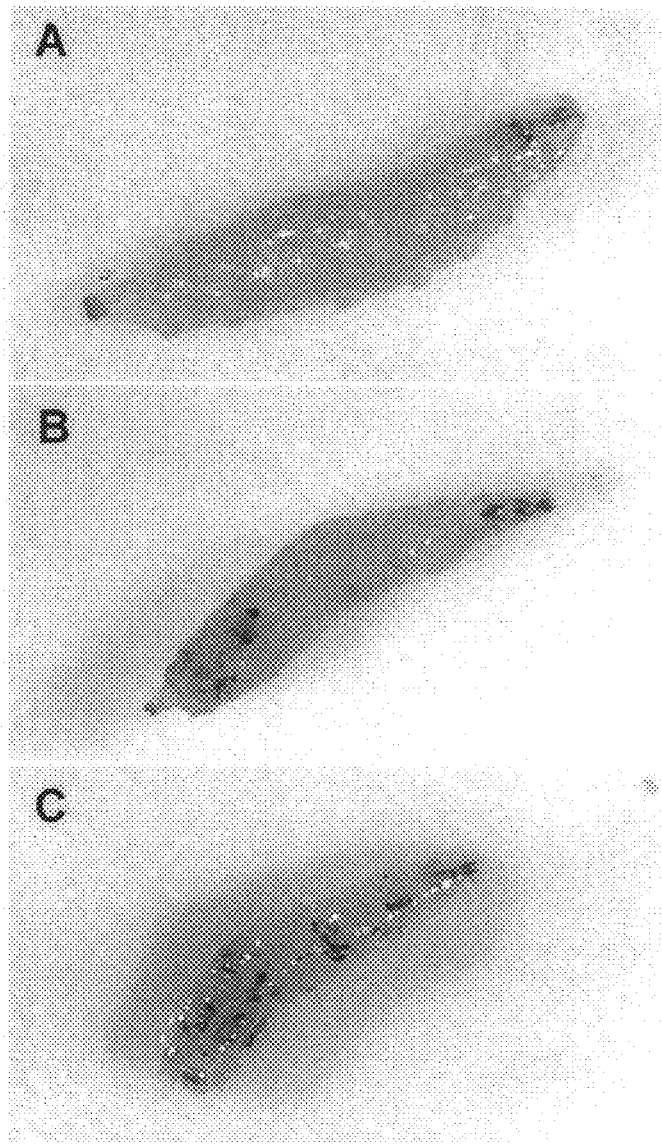
FIG. 1A provides a computer generated representation of a wild type larva.
FIG. 1B provides a computer generated representation of a tumorous larva according to the subject invention.
FIG. 1C also provides a computer generated representation of a tumorous larva according to the subject invention.

Non-mammalian transgenic animals, particularly insects, e.g. flies, that have neoplastic phenotypes are provided. The subject transgenic animals are characterized in that they spontaneously develop metastatic tumors. The subject animals comprise a v-myb transgene that is expressed in a manner that gives rise to the neoplastic phenotype. Also provided are methods of using the subject non-mammalian transgenic animals to screen for compounds having activity with respect to cellular proliferative diseases, particularly compounds that are therapeutic for neoplastic diseases. In further describing the subject invention, the transgenic animals and methods for their production will be detailed first, followed by a discussion of the screening methods of the subject invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

ANIMAL MODELS

The invention provides non-mammalian animal models that exhibit a neoplastic phenotype, where the phenotype results from the expression of a transgene in the proper spatial manner, as described in greater detail below. By neoplastic phenotype is meant that the subject transgenic non-mammalian animal models spontaneously develop metastatic tumors at some point during their life-span. Thus, a particular multicellular organism is a transgenic animal according to the subject invention no matter which stage of development it is at, so long as the animal spontaneously develops metastatic tumors (at least one) at some point during its lifetime. Transgenic animals having the neoplastic phenotypic characteristics of the subject invention are readily identified, as they have the following phenotypic characteristics: (1) development of dark colored, dense clusters of dividing cells at some point during their lifetime, where the clusters (or a portion thereof) can be dissected from the transgenic animal and grown in culture, where the size of the culture grown cluster of cells doubles in about 4 to 10 days, usually about 5 to 7 days; and (2) transplantation of the tumors from the subject transgenic animals into normal recipients, e.g. larva, tends to induce death.

The transgenic animals of the subject invention are non-mammalian transgenic animals. Of particular interest are invertebrate transgenic animals, particularly members of the phylum arthropoda, and more particularly members of the class insecta. Of particular interest in many embodiments are transgenic flies. In many preferred embodiments, the transgenic flies are members of the family Drosophilidae, where the transgenic animal is often a *Drosophila melanogaster*. The subject invention is now further described in terms of transgenic flies.

A critical feature of the subject transgenic animals is that the animals harbor a stably integrated transgene that is spatially expressed in a manner sufficient to result in the desired neoplastic phenotype. The term "transgene" is used herein to describe genetic material which has been or is about to be artificially inserted into the genome of a cell. With regards to spatial expression of the transgene, expression is generally limited to the amnioserosa and peripheral nervous system.

The transgene encodes a product that, when expressed in the appropriate spatial manner, gives rise to the neoplastic phenotype. As mentioned above, the transgene is a v-myb gene, where the v-myb gene may be the naturally occurring v-myb gene or a gene that encodes a product which, though not identical to the product encoded by the naturally occurring v-myb gene, nonetheless gives rise to the neoplastic phenotype. Thus, the transgene may comprise a nucleic acid having the sequence of the naturally occurring v-myb gene or a sequence that includes only a v-myb domain. As such, the transgene at least includes a v-myb domain or a sequence that is substantially similar to a domain found in the naturally occurring v-myb, where substantially similar means a nucleic acid sequence having a sequence identity with a naturally occurring v-myb domain of at least about 50%, usually at least about 60% and more usually at least about 65%, where sequence identity is determined using the BLAST program at default settings (using default settings, i.e. parameters w=4 and T=17). In many embodiments, the transgene comprises a naturally occurring v-myb gene or a sequence substantially similar thereto, where viral myb genes of interest include that induce oncogenesis in vertebrates, such as: v-myb-1151 as described in Fu, S. L. and J. S. Lipsick (1996) J. Vir. 70: 5600–5610; AMV-vmyb, E26 vmyb, dGE vmyb, and 1183 vmyb where each of these is described in Ganter & Lipsick, Adv. Cancer Res. (1999) 76:21–60, and the references disclosed therein.

The v-myb transgene is stably integrated into the genome of the animal in manner such that its expression is controlled spatially to the desired cell type. Specifically, the subject transgene is stably integrated into the genome of the animal under the control of a promoter that provides for expression in at least the amnioserosa and/or peripheral nerve system. The transgene may be under the control of any convenient promoter that provides for this requisite spatial expression pattern, where the promoter may be endogenous or exogenous, but will generally be endogenous. A suitable promoter is the promoter located on the $4^{th}$ chromosome in the Drosophila melanogaster genome that regulates GAL4 expression in stock #3737 (Bloomington, Ind. designation).

The transgene may be integrated into the fly genome in a manner that provides for direct or indirect expression activation by the promoter, i.e. in a manner that provides for either cis or trans activation of gene expression by the promoter. In other words, expression of the transgene may be mediated directly by the promoter, or through one or more transactivating agents. Where the transgene is under direct control of the promoter, i.e. the promoter regulates expression of the transgene in a cis fashion, the transgene is stably integrated into the genome of the fly at a site sufficiently proximal to the promoter and in frame with the promoter such that cis regulation by the promoter occurs.

In yet other embodiments where expression of the transgene is indirectly mediated by the endogenous promoter, the promoter controls expression of the transgene through one or more transactivating agents, usually one transactivating agent, i.e. an agent whose expression is directly controlled by the promoter and which binds to the region of the transgene in a manner sufficient to turn on expression of the transgene. Any convenient transactivator may be employed, where the GAL4 transactivator system is particularly preferred in many embodiments of the subject invention.

In these preferred embodiments of the subject invention in which the transgenic fly comprises the GAL4 targeted expression system, a GAL4 encoding sequence is stably integrated into the genome of the animal in a manner such that it is operatively linked to the endogenous promoter that provides for expression in the appropriate spatial and temporal manner. An example of such a fly is fly line #3734 available from the Bloomington Stock Center (Bloomington, Ind.)(http://flybase.bio.indiana.edu/). The transgene is stably integrated into a different location of the genome, generally a random location in the genome, where the transgene is operatively linked to an upstream activator sequence, i.e. UAS sequence, to which GAL4 binds and turns on expression of the transgene. Transgenic flies having a UAS: GAL4 transactivation system are known to those of skill in the art and are described in Brand & Perrimon, Development (1993) 118: 401–415; and Phelps & Brand, Methods (April 1998) 14:367–379.

METHODS OF PRODUCING THE SUBJECT TRANSGENIC FLIES

The subject transgenic flies can be prepared using any convenient protocol that provides for stable integration of the transgene in to the fly genome in a manner sufficient to provide for the requisite spatial expression of the transgene, i.e. in mainly the amnioserosa and peripheral nervous system. A number of different strategies can be employed to obtain the integration of the transgene with the requisite expression pattern. Generally, methods of producing the subject transgenic flies involve stable integration of the transgene into the fly genome. Stable integration is achieved by first introducing the transgene into a cell or cells of the fly, e.g. a fly embryo. The transgene is generally present on a suitable vector, such as a plasmid. Transgene introduction may be accomplished using any convenient protocol, where suitable protocols include: electroporation, microinjection, vesicle delivery, e.g. liposome delivery vehicles, and the like. Following introduction of the transgene into the cell(s), the transgene is stably integrated into the genome of the cell. Stable integration may be either site specific or random, but is generally random.

Where integration is random, the transgene is typically integrated with the use of transposase. In such embodiments, the transgene is introduced into the cell(s) within a vector that includes the requisite P element, terminal 31 base pair inverted repeats. Where the cell into which the transgene is to be integrated does not comprise an endogenous transposase, a vector encoding a transposase is also introduced into the cell, e.g. a helper plasmid comprising a transposase gene, such as pTURBO (as disclosed in Steller & Pirrotta, "P Transposons Controlled by the Heat Shock Promoter," Mol. Cell. Biol. (1986) 6:1640–1649). Methods of random integration of transgenes into the genome of a target Drosophila melanogaster cell(s) are disclosed in U.S. Pat. No. 4,670,388, the disclosure of which is herein incorporated by reference.

In those embodiments in which the transgene is stably integrated in a random fashion into the fly genome, means are also provided for selectively expressing the transgene at the appropriate time during development of the fly. In other words, means are provided for obtaining targeted expression of the transgene. To obtain the desired targeted expression of the randomly integrated transgene, integration of particular promoter upstream of the transgene, as a single unit in the P element vector may be employed. Alternatively, a transactivator that mediates expression of the transgene may be employed. Of particular interest is the GAL4 system described in Brand & Perrimon, supra.

In this particular embodiment, the subject transgenic flies are produced by: (1) generating two separate lines of transgenic flies: (a) a first line that expresses GAL4 in mainly the amnioserosa and peripheral nervous system, e.g. under the control the endogenous fly promoter located on the $4^{th}$ chromosome (as found in fly line #3734 described supra); and (b) a second line in which the transgene is stably integrated into the cell genome and is fused to a UAS domain; (2) crossing the two lines; and (3) screening the progeny for the desired phenotype, i.e. spontaneous development of neoplastic tumors. Each of the above steps is well known to those of skill in the art. See e.g. Brand & Perrimon, Development (1993) 118: 401–415; and Phelps & Brand, Methods (April 1998) 14:367–379. See also the Experimental Section, infra.

The above strategy is employed to obtain fertilized eggs that comprise the transgene stably integrated into the genome in a manner such that it is expressed in the correct spatial and temporal manner so that the eggs give rise to adult flies exhibiting the desired neoplastic phenotype. Generally, the fertilized eggs are allowed to mature under conditions that give rise to the neoplastic phenotype.

The neoplastic phenotype of the animals can be tailored by varying the conditions under which the animals are allowed to mature. For example, temperature can be employed to modulate the nature neoplastic phenotype of the subject animals. Rearing the embryos/larva at 30–31° C. induces metastatic tumors in all larva, while rearing at 28° C. results in few larva generate metastatic tumors. Rearing at 22–24° C. results in the majority of the larva having metastatic tumors. Finally, growth at 18° C. results in few larva that generate tumors, but the larva that do generate tumors have extremely metastatic tumors.

UTILITY

The subject flies find use in a variety of applications, including: as tools for use in the elucidation of genetic mechanisms involved in cellular proliferative disorders; as a screening tool that identifies therapeutic compounds for use in the treatment of cellular proliferative conditions (e.g. as animal models for human neoplastic disease conditions); and as tools for use in the identification neoplastic gene targets, i.e. genes whose expression can be modulated, e.g. enhanced or disrupted, in order to alleviate a neoplastic condition. The subject transgenic flies find particular use in screening methods designed to identify therapeutic agents for use in the treatment of neoplastic diseases.

Screening Methods

As mentioned above, the subject transgenic flies find particular utility in screening assays designed to identify therapeutic compounds for cellular proliferative conditions, particularly neoplastic conditions. Through use of the subject transgenic flies (or cells derived therefrom depending on the particular screening assay), one can identify compounds that have activity with respect to a neoplastic disease. Compounds have activity with respect to a neoplastic disease if they modulate or have an effect on at least one parameter or symptom of the disease, such as loss abnormal cell division or complications associated therewith, where the modulatory activity may be to reduce or enhance the magnitude of the symptom, depending on the nature of the disease and the symptom. Thus, the screening methods of subject invention can be used to identify compounds that modulate the progression of neoplastic diseases, e.g. by binding to, modulating, enhancing or repressing the activity of a protein or peptide involved in the progression of the neoplastic disease, and/or compounds that ameliorate, alleviate or ever remove the phenotypic symptoms of the disease, where such activity may or may not be the result of activity with respect to the underlying mechanism of the disease. Screening to determine drugs that lack effect on the neoplastic condition is also of interest. Assays of the invention make it possible to identify compounds which ultimately: (1) have a positive affect with respect to a neoplastic disease condition and as such are therapeutics, e.g. agents which arrest or reverse the neoplastic condition or ameliorate or alleviate the symptoms of such a condition; or (2) have an adverse affect with respect to the neoplastic disease and as such should be avoided as therapeutic agents.

In the screening methods of the subject invention, a quantity of a candidate agent is generally orally administered to the fly. Following oral administration, the affect of the candidate agent on the metastatic tumors (or appearance thereof) of the fly is determined. typically by comparison with a control (i.e. a transgenic fly to which the candidate agent has not been administered). The affect of the candidate agent is determined by determining whether one or more of the phenotypic characteristics of the neoplastic condition are exacerbated or ameliorated in the test fly as compared to the control fly, where characteristics that are monitored include tumor growth, tumor metastasis, and the like. The candidate agent is generally orally administered to the fly by mixing the agent into the fly nutrient medium, e.g. water, aqueous solution with additional nutrient agents, etc., and placing the medium in the presence of the fly, (either the larva or adult fly, usually the adult fly) such that the fly feeds on the medium. Generally a plurality of assay mixtures are run in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel using a large number of flies. By "large number" is meant a plurality, where plurality means at least 10 to 50, usually at least 100, and more usually at least 1000, where the number of may be 10,000 or 50,000 or more, but in many instances will not exceed 5000.

Of particular interest in certain embodiments is the use of the subject flies in a high throughput toxicity screening assays, as described in U.S. patent application Ser. No. 60/147,220 filed Aug. 4, 1999, the disclosure of which is herein incorporated by reference. In such high throughput screening assays, a plurality of different compound compositions, usually at least 10 different compound compositions, are simultaneously assayed for their toxic activity, if any. Each compound composition in the plurality is assayed for toxicity by contacting it with a population of the subject transgenic animals having a neoplastic phenotype and determining the effect of the compound composition on the animals. Such HTS methods find particular use in finding agents for use in the treatment of cellular proliferative diseases, e.g. neoplastic diseases, as only those compounds that treat the disease and yet are sufficiently non-toxic to allow the animal to live are identified as positives for further study.

The subject methods find use in the screening of a variety of different potentially therapeutic candidate agents. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Screening may be directed to known pharmacologically active compounds and chemical analogs thereof, or to new agents with unknown properties such as those created through rational drug design. Candidate agents having therapeutic activity with respect to the neoplastic condition can be identified based on their ability to at least ameliorate, if not completely alleviate or remove, one or more of the neoplastic phenotypes of the adult transgenic fly of the subject invention, such as tumor growth, tumor metastasis, and the like, as described above.

Of particular interest is the use of the subject screening methods to identify cancer therapeutic agents that exhibit low host toxicity and yet are effective as antineoplastic agents. Tradition chemotherapy and radiation treatments affect normal and tumor cells alike. The tolerance for normal cells is high because the primary mechanism of these treatments affect only dividing cells and since the majority of normal cells are not dividing the side effects are tolerated, but still quite severe. The subject screening methods place a high stringency on side effects as a significant amount of cell division is required for the larva to develop into a viable fly. Therefore the anti-metastatic tumor compounds selected by the subject screening methods will have to be highly specific to kill or inhibit tumor formation/growth/metastisis, otherwise the developing fly will die. In other words, the subject methods represent a sensitive system for selecting antitumor drug candidates that also have low toxicity to normal developing and dividing cells.

The above screening methods may be part of a multi-step screening process of evaluating candidate therapeutic agents for their efficacy (and safety) in the treatment of neoplastic diseases in mammalian hosts, e.g. humans. In multi-step screening processes of the subject invention, a candidate compound or library of compounds is subjected to screening in a second in vivo model, e.g. a mouse model, following screening in the subject transgenic animal model. Following the initial screening in the non-mammalian transgenic animals of the subject invention, the positive compounds are then screened in non-human mammalian animal models, including transgenic non-human mammalian animal models. Transgenic mouse models of neoplastic diseases and methods for their use in screening assays are described in: U.S. Pat. Nos. 5,917,124; 5,907,078; 5,849,996; 5,709,844; 5,550,316; and 4,736,866, the disclosures of which are herein incorporated by reference. In addition, a pre in vivo screening step may be employed, in which the compound is first subjected to an in vitro screening assay for its potential as a therapeutic agent in the treatment neoplastic conditions. Any convenient in vitro screening assay may be employed, where a variety of suitable in vitro screening assays are known to those of skill in the art.

Identification of Gene Targets

In addition to their use as animal models for screening candidate therapeutic agents, the subject transgenic flies also find use in the identification of neoplastic gene targets, i.e. genes whose expression can be beneficially modulated to treat neoplastic diseases. Gene based therapies can be identified by doing traditional enhancer/suppressor analyses in the subject transgenic flies. In these analyses, genes in the subject transgenic flies are mutated to identify ones that either exacerbate or alleviate the neoplastic phenotype. Methods of mutating genes and carrying out enhancer/ suppressor analyses are well known to those of skill in the art (Hays, T S et al., Molecular and Cellular Biology (March 1989) 9(3):875–84; Deuring, R; Robertson, B; Prout, M; and Fuller, M T. Mol. Cell. Biol., 1989 9:875–84.; Fuller, M T et al., Cell Mot. Cyto. (1989) 14 :128–35; Rottgen G, Wagner T, Hinz U Mol. Gen. Genet. 1998 257:442–51).

Genes that mutate to enhance the neoplastic phenotype in a recessive manner yield potential protein therapeutics for neoplastic conditions, since elevating the normal gene product level of such genes potentially alleviates the neoplastic condition. Genes that mutate to suppress the neoplastic condition in a recessive manner yield gene targets for disruption to alleviate the neoplastic conditions, where disruption of these genes can be achieved using a variety of methods, ranging from deleting the DNA for the target gene to inhibiting its transcription, translation, or protein activity. For screening candidate agents, small molecule antagonists to these genes can be constructed and evaluated for efficacy in the fly model through oral administration. Alternatively, large molecular antagonists can be delivered by gene therapy, as described infra.

KITS

Also provided by the subject invention are kits for use in performing the subject screening methods. The subject kits include at a plurality of transgenic flies of the subject invention, or a means for producing such a plurality of flies, e.g. a male and female transgenic fly of the subject invention, vectors carrying requisite genes, such as the transgene, a transposase gene, GAL4, etc. The flies may be housed in appropriate container(s), e.g. vials. The subject kits may also comprise a nutrient medium for the animals, e.g. drosophila medium.

THERAPEUTIC AGENTS AND PHARMACEUTICAL COMPOSITIONS

Also provided by the subject invention are therapeutic agents for use in treating a neoplastic condition, as well as pharmaceutical formulations thereof. The therapeutic agents of the subject invention are those agents identified using the screening methods described supra that show beneficial activity with respect to a neoplastic condition (or agents known to have an effect on the expression of a gene identified as modulating the phenotype of a neoplastic condition, where identification employs the use of the subject non-transgenic animals).

Also provided are pharmaceutical compositions of the subject therapeutic agents. In the pharmaceutical compositions or formulations of the subject invention, agents described above are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof (as identified using the mutant screen analysis protocols described supra, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

METHODS OF TREATING NEOPLASTIC CONDITIONS

Also provided are methods of treating cellular proliferative disease conditions, particularly neoplastic disease conditions, using the subject active agents. In the subject methods, an effective amount of the active agent of the subject invention is administered to the host to be treated. By "effective amount" is meant a dosage sufficient to produce a desired result, where the desired result is generally an amelioration or alleviation, if not complete cessation, of one or more symptoms of the cellular proliferative disease being treated. Administration of the agents can be achieved in various ways, including oral, buccal, rectal, parenteral, intraperitoneal, intradernal, transdermal, intracheal, etc. A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The following examples are offered by way of illustration and not by way of limitation.

EXPERIMENTAL

A. Preparation of flies containing the pUAST-v-myb-1151 construct

The v-myb-1151 gene (as described in Fu and Lipsick, 1996, supra) was cloned into the polylinker of the pUAST such that the UAS vector sequences were adjacent to the 5' end of the myb gene (Brand et al. 1993, supra). Transcription of the construct was controlled by GAL4, which needs to bind to the UAS sequence to drive expression of the gene that has been cloned into the pUAST vector. The pUAST-v-myb-1151 construct was integrated into the genome of Drosophila melanogaster by standard microinjection procedures (Spradling, A. C., and Rubin, G. M. (1982). Science 218, 341–347). The transposase source used to stimulate the integration of the pUAST-myb-1151 construct into the genome was provided by co-injecting the vector pTURBO (as described in Steller & Pirrotta, (1986) supra).

B. Production of flies having a neoplastic phenotype

Flies containing the pUAST-v-myb-1151 construct were mated to the #3734 GAL4 producing fly strain (as described in Brand (1993) supra) and obtained from the Bloomington stock center in Indiana (http://flybase.bio.indiana.edu/) and their progeny were allowed to develop.

TABLE 1

Phenotypes of Tumor Afflicated Larva over a Temperature Range

| Temperature (C.) | % of larva with 1+ tumors | % of larva with 2+ tumors |
|---|---|---|
| 18 | 6 | 6 |
| 22 | 70 | 58 |
| 28 | 36 | 4 |
| 30–31 | 100 | 100 |

Larva = third instar larva
The number scored for each temperature = 50

The resultant flies spontaneously produced tumors. See FIGS. 1A to 1C. Tumors (dark colored, dense clusters of dividing cells) were dissected from the animals and their growth was examined in culture. Standard insect cell culture media was used (Sigma-Aldrich) and cells were incubated at 22° C. The volume of the tumor doubled in 5 to 7 days. Furthermore, our studies suggest that normal larva are killed by receiving a tumor transplant. These results indicate that these are classical tumors that are being generated in the v-myb expressing fruit fly.

| Transplantation of tumors into normal larva | |
|---|---|
| | viable flies |
| Mock Surgery | 33.3% |
| Tumor Surgury | 7.8% |

The number of scorable mock surguries performed = 54
The number of scorable tumor surguries performed = 51

A scorable surgery is one where post operation the larva moves normally and no internal fluid leaks out from the incision.

C. Screening Assays

A variety of herbs and Chinese medicines have been identified for having antitumor activity. Those in Table 2 have activity against a variety of cancer types, which includes: hepatic, colon, leukemia, lymphoma, glioma, breast, prostate, pancreas, bladder, melanoma, arid lung. See e.g. Zheng, et al. Immunopharmacol Immunotoxicol 1995. 17: 69–79; Borchers, et al., Proc. Soc. Exp. Biol. Med. 1999. 221: 281–293; Hu, et al., Planta Med 1996. 62: 573–575; Zheng, et al., J. Cell Biochem. Suppl. 1997. 27: 106–112; Nakahata, et al., J. Chin. Med. 1998. 26: 311–23; Kato, et al., J. Invest. Dermatol. 1998. 111: 640–644; Huang, et al., J. Med. 1997. 46:132–137;Yamashiki, et al., J. Gastroenterol. Hepatol. 1996. 11: 137–142; Sakamoto, et al. Am. J. Chin. Med. 1994. 22: 43–50; Ito & Shimura, Jpn. J. Pharmacol. 1986. 41: 307–314; Michaud, et al. J. Natl. Cancer Inst. 1999. 91: 605–613; Sasaki, et al. Nutr. Cancer 1999. 33: 76–81; Sengupta & Das, Eur. J. Cancer Prev. 1999. 8: 325–330. The extract concentration fed to the larva/fly that delayed tumor progression by 20% or more is indicated in Table 2. Furthermore, drugs treating this condition appear to be specific for antitumor properties as random extracts fed to the flies identify a positive ~ 0025% of the time.

TABLE 2

Extracts of herbs and Chinese medicines that are known to have antitumor activity in mammals show a similar activity in our tumor fly model

| Extract tested for antitumor activity | Positive antitumor activity dose range |
| --- | --- |
| Ginkgo biloba leaf | .01%–100% |
| Trichosanthes | 10%–100% |
| Grifola | 10%–100% |
| Dioscorea | .01%–.1% |
| *Rhizoma zedoariae* | 1%–100% |
| Broccoli | .01%–100% |
| Lycopene | .01%–100% |
| Sho Saiko to | .01%–.1% |

The ability of known chemicals to affect the tumors in this mutant fly strain indicates that it is a capable of identifying chemicals that will be beneficial for treating human cancers. As the tumors in this mutant fly strain are affected by chemicals that target a variety of tumor types in mammals, these fly tumors are a primitive generic tumor. That is, this tumor has the basic properties of cancer, however lacking the more sophisticated mechanisms associated with specific organ/tissues in mammals. For example, flies do not possess breast or pancreas tissues. However, these tumors are inhibited by chemicals that target breast and pancreas tumor types. As such, at least some of the fundamental properties are the same in both the fly tumors as well as pancreas and breast cancers. Therefore, the subject flies have uncovered tumor progression pathways that are common for most cancers.

It is evident from the above results and discussion that the subject invention provides a valuable screening tool for use in the evaluation of potential therapeutic agents for use in the treatment of cellular proliferative disorders. Advantages of using the subject transgenic flies for screening potential therapeutic candidates include: adaptability of the subject flies to high throughput screening protocols, simplicity and low cost of maintaining the subject flies, ability of the subject flies to identify potentially orally active therapeutic agents, rapid reproduction of the subject flies, and ability of the subject flies to produce large numbers of offspring. Accordingly, the subject invention fills a void in the existing arsenal of screening tools, in that the subject invention provides a means for conducting in vivo high throughput screening assays. A further significant advantage is the ability to use the subject flies to identify compounds that exhibit low or no toxicity to normal dividing cells but still exhibit sufficient toxicity to abnormally dividing cells. As such, the subject screening methods provide a means for identifying effective anti-neoplastic agents that exhibit low or no toxicity to normal cells. Therefore, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A transgenic *Drosophila melanogaster* whose genome comprises a v-myb transgene, wherein an endogenous amnioserosa and peripheral nervous system specific promoter drives the expression of v-myb, wherein said v-myb transgene is expressed in the amnioserosa and peripheral nervous system and wherein expression of said v-myb transgene results in the development of metastatic tumors in said transgenic *Drosophila melanogaster.*

2. A method of screening a candidate compound for an anti-neoplastic activity, wherein said method comprises:
   administering said candidate compound to the transgenic Drosophila melanogaster of claim 1;
   measuring an effect of said candidate compound on growth of a metastatic tumor in said transgenic *Drosophila melanogaster;*
   comparing growth of the metastatic tumor in said transgenic *Drosophila melanogaster* with the growth of the metastatic tumor in a control transgenic *Drosophila melanogaster* that did not receive said candidate compound, wherein a decrease in the growth of the metastatic tumor is indicative of the anti-neoplastic activity of the candidate compound.

3. The method according to claim 2, wherein said candidate compound is orally administered to said transgenic *Drosophila melanogaster.*

4. A method of screening a candidate compound for an anti-neoplastic activity, wherein said method comprises:
   feeding said compound to the transgenic *Drosophila melanogaster* of claim 1; measuring an effect of said candidate compound on growth of a metastatic tumor in said transgenic *Drosophila melanogaster;*
   comparing growth of the metastatic tumor in said transgenic *Drosophila melanogaster* with the growth of the metastatic tumor in a control transgenic *Drosophila melanogaster* that did not receive said candidate compound, wherein a decrease in the growth of the metastatic tumor is indicative of the anti-neoplastic activity of the candidate compound.

5. The method according to claim 4, wherein said candidate compound is present in a nutrient medium.

6. The method according to claim 4, wherein said method further comprises screening at least a second candidate compound for an anti-neoplastic activity by:
   feeding said second compound to a second transgenic *Drosophila melanogaster* of claim 1;
   measuring an effect of said second candidate compound on growth of a metastatic tumor in said second transgenic *Drosophila melanogaster*; and
   comparing growth of the metastatic tumor in said second transgenic *Drosophila melanogaster* with the growth of the metastatic tumor in said control transgenic *Drosophila melanogaster* that did not receive said candidate compound, wherein a decrease in the growth of the metastatic tumor is indicative of the anti-neoplastic activity of the second candidate compound.

7. The method according to claim, 6, wherein said second candidate compound is present in a nutrient medium.

8. A method of identifying a gene that potentially modulates the growth of a metastatic tumor, wherein said method comprises:
   (a) producing a mutation in the genome of the transgenic *Drosophila melanogaster* of claim 1;
   (b) determining whether said mutation has an effect on the growth of a metastatic tumor in said transgenic *Drosophila melanogaster;*

(c) identifying the gene in which the mutation was produced in step (a), wherein the identified gene of step (c) potentially modulates the growth of a metastatic tumor if the mutation in the gene had an effect on the growth of said metastatic tumor in said transgenic *Drosophila melanogaster*.

9. The method according to claim 8, wherein said effect is an increase in the growth of the metastatic tumor.

10. The method according to claim 8, wherein said effect is a decrease in the growth of the metastatic tumor.

* * * * *